(12) United States Patent
Wang et al.

(10) Patent No.: US 6,686,209 B2
(45) Date of Patent: Feb. 3, 2004

(54) REAGENTS FOR DETECTING CANNABINOIDS

(75) Inventors: Guohong Wang, Rancho Cucamonga, CA (US); Thomas Foley, Rancho Cucamonga, CA (US); Connie Chang, Rancho Cucamonga, CA (US); Greg Liang, Rancho Cucamonga, CA (US); Albert Avila, Rancho Cucamonga, CA (US)

(73) Assignee: Lifepoint, Inc., Ontario, CA (US)

( * ) Notice: Subject to any disclaimer, the term of this patent is extended or adjusted under 35 U.S.C. 154(b) by 242 days.

(21) Appl. No.: 09/805,469

(22) Filed: Mar. 12, 2001

(65) Prior Publication Data

US 2002/0142484 A1 Oct. 3, 2002

(51) Int. Cl.[7] .................. G01N 33/533; G01N 33/534; G01N 33/535; G01N 33/553; G01N 33/538
(52) U.S. Cl. .............. 436/546; 435/7.93; 436/525; 436/532; 436/534; 436/541; 436/542; 436/544; 436/545; 436/815; 436/501
(58) Field of Search ................. 435/188, 7.93; 436/544, 545, 546, 815, 525, 532, 534, 541, 542, 501

(56) References Cited

U.S. PATENT DOCUMENTS

| 5,219,747 A | 6/1993 | McNally et al. ............ 435/188 |
| 5,264,373 A | 11/1993 | Wang et al. ................ 436/537 |

FOREIGN PATENT DOCUMENTS

EP 0 736 529 A1 9/1996

OTHER PUBLICATIONS

Derwent Abstract 1992–147594 (1992).*
S. Salamone et al, J. Forensic Sci., 43(4), 821–826 (1998).*
B. Law et al, J. Forensic Sci. Soc., 22(3), 275–281 (1982).*
H. Tanaka et al, Forensic Sci. Int., 106(3), 135–146 (1999).*
M. Elsohly et al, J. Anal. Toxicol., 14(5), 277–279 (1990).*

* cited by examiner

*Primary Examiner*—Mary E. Ceperley
(74) *Attorney, Agent, or Firm*—Jones Day

(57) ABSTRACT

In this disclosure, novel caanabinol-based tracers suitable for use in immunoassays that detect cannabinoids in a biological sample are disclosed. These cannabinol-based tracers are particularly useful in a continuous flow displacement immunoassay. The disclosure also describes the processes for synthesizing the novel tracers, and the application of these tracers in fluorescence immunoassays for detecting and quantifying cannabinoids in biological samples.

61 Claims, 8 Drawing Sheets

Method A:
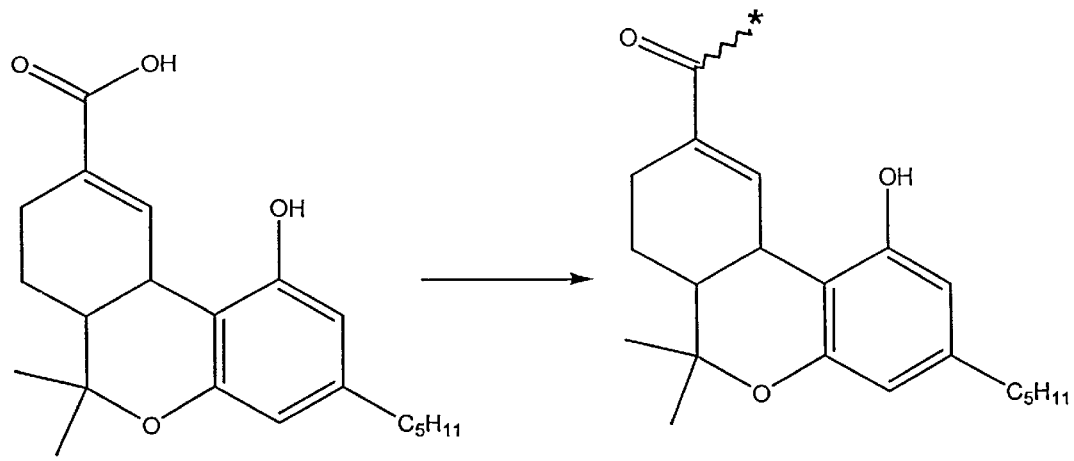
Method B:
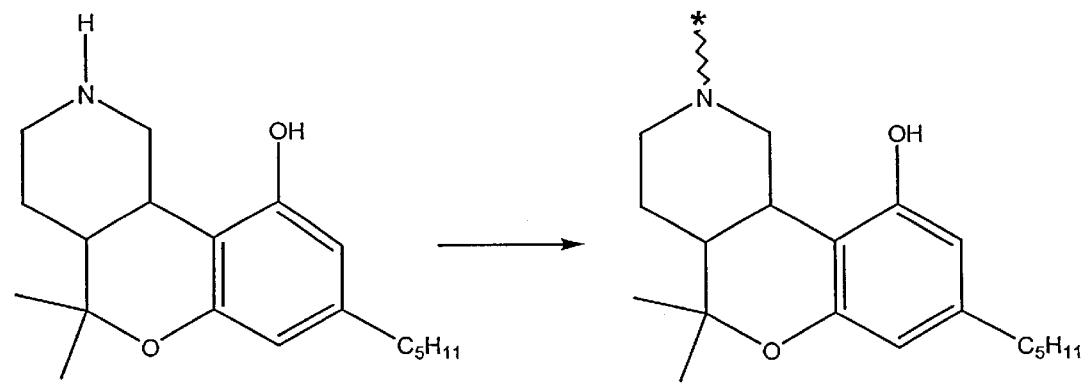
Fig. 1

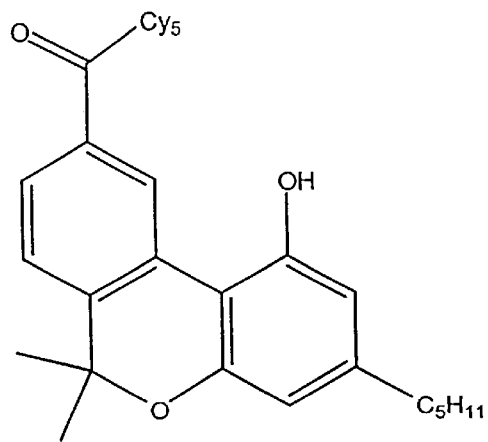
Fig. 10 Tracer GW6-25
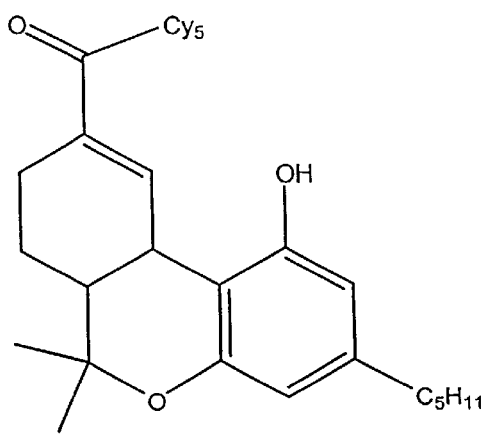
Fig. 11 GW5-51
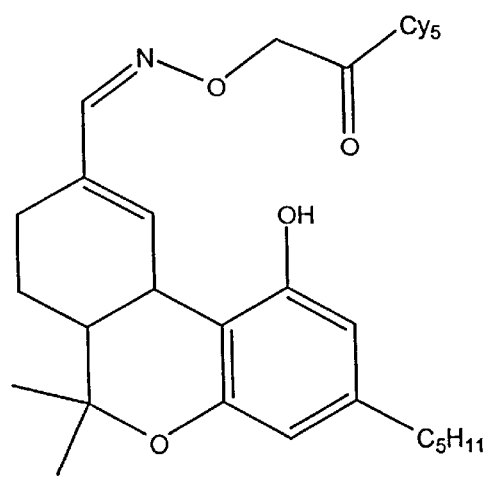
Fig. 12 Tracer Gw2-82

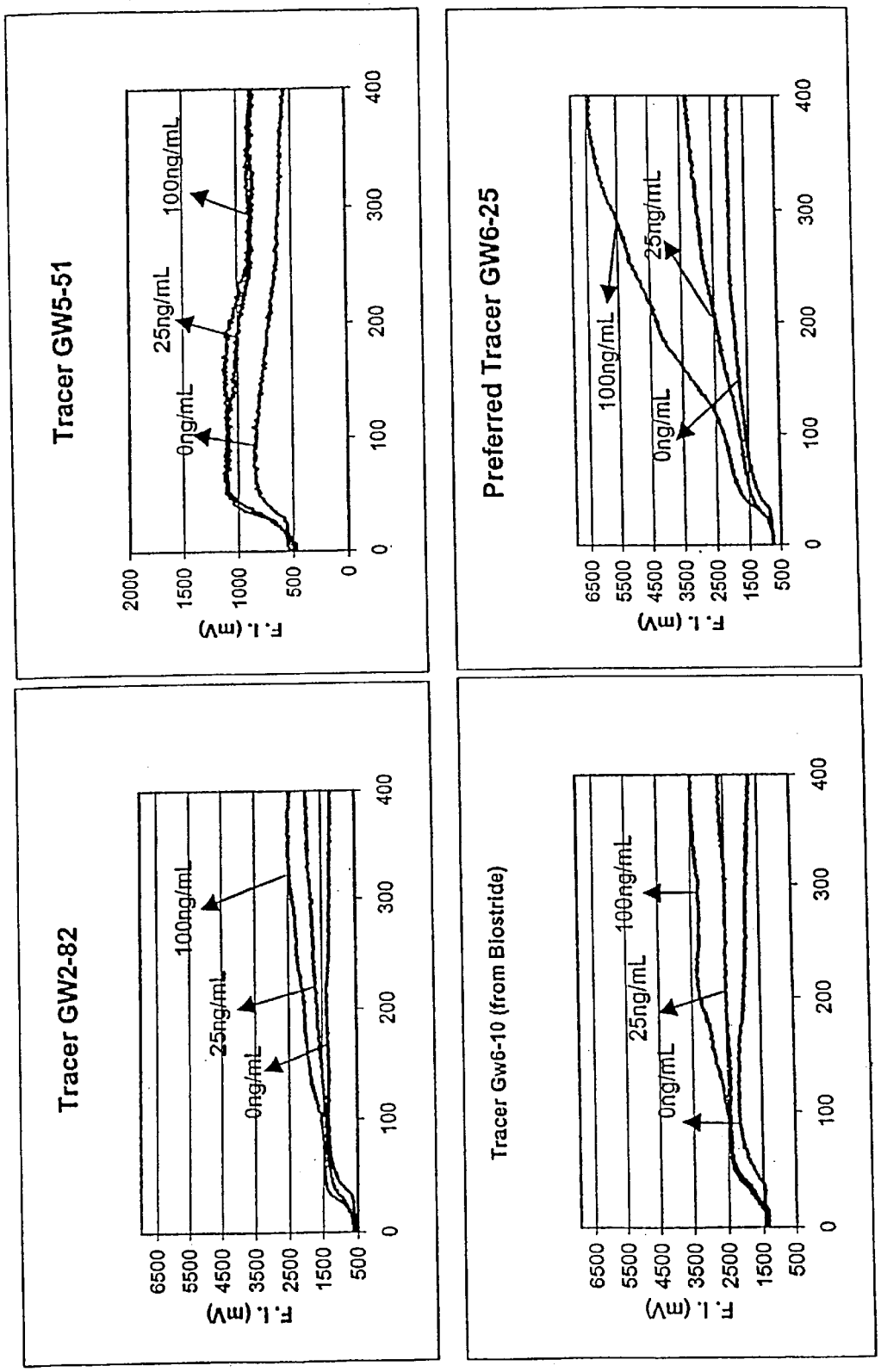
Fig. 13 Comparison of the Effect of Varied Tracers on Continuous Flow Displacement Immunoassay of $\Delta^9$-THC (Ab:Tr=1:1.2)

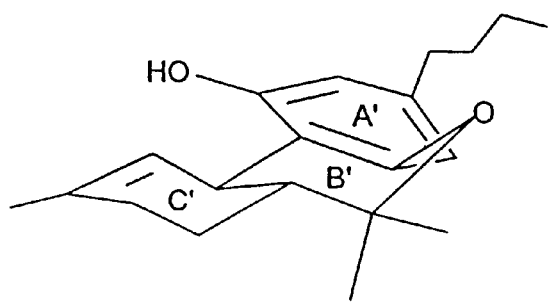
Δ⁹-THC
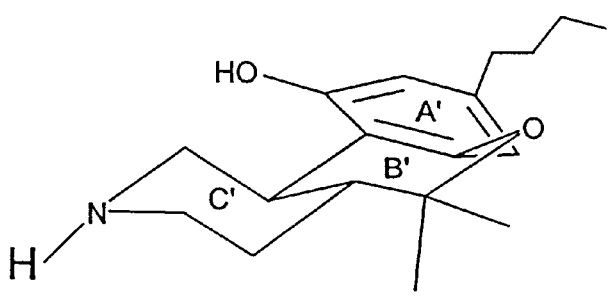
THC Analog
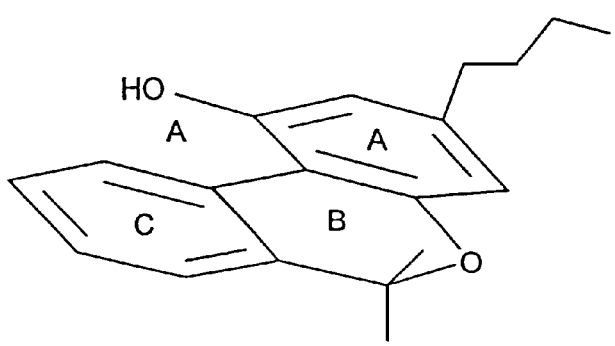
Cannabinol
Fig. 14

US 6,686,209 B2

REAGENTS FOR DETECTING CANNABINOIDS

FIELD OF THE INVENTION

The field of the present invention relates to the detection of controlled substances. In particular, it relates to labeled tracers for use in detecting cannabinoids and tetrahydrocannabinoids (THC) in biological samples.

BACKGROUND OF THE INVENTION

Marijuana, a known psychoactive drug, is derived from plants of the hemp family that produce significant amounts of cannabinoids. In particular, the most important cannabinoid is $\Delta^9$-tetrahydrocannabinol ($\Delta^9$-THC), the major physiologically active constituent of marijuana. $\Delta^9$-THC is a controlled substance because it has both sedative and depressant-like effects on the cardiovasular and central nervous systems, as opposed to cannabidiol, a non-psychoactive constituent of marijuana. Through smoking marijuana, $\Delta^9$-THC is rapidly absorbed from the lungs into the blood stream and metabolized through 11-nor-$\Delta^9$-THC to a series of polar metabolites with 11-nor-$\Delta^9$-THC-carboxylic acid as the primary metabolite.

Due to the common abuse of cannabinoids, there is a growing need for non-invasive and rapid tests to detect the presence of these controlled drugs in biological specimens. Currently, cannabinoids in biological samples can be detected by a number of techniques such as thin layer chromatography (TLC), gas chromatography/mass spectrometry (GC/MS), radioimmunoassay or enzyme immunoassay. Depending upon assay sensitivity, cannabinoid metabolites may be detected in the urine for up to 10 days in occasional smokers and 36 days in chronic smokers. See Wang et al, U.S. Pat. No. 5,264,373, col 1, lines 36–37.

In recent years, there have been many reports concerning the use of saliva for drug monitoring. Saliva testing for the presence of $\Delta^9$-THC has been applied to pharmacokinetic studies or to the management of patients in chronic drug therapy. See Samyn, et al, *Forensic Science Review*, vol. 11, p. 1, (1999). Although saliva testing does not quantify the blood concentration of the drug, (See Gross et al, "Validated Direct Blood 9-THC Radioimmunoassay Quantitation", *J. Anal. Toxi.* Vol.2, p.98 (1978)), saliva testing is of particular interest since the presence of $\Delta^9$-THC in the saliva may indicate recent smoking of cannabinoids. The concentration of $\Delta^9$-THC in the blood may also be estimated from the concentration of $\Delta^9$-THC; the blood concentration is usually much higher than the drug concentration in saliva. Idowu, et al, "A Review of the Use of Saliva in the Forensic Detection of Drugs and Other Chemicals", J. Forensic Science Society, v22, 1982, p123.

Furthermore, the use of a continuous flow displacement immunoassay technology (F. S. Ligler, et al, Flow Immunosensor Method and Apparatus, U.S. Pat. No. 5,183,740) has been demonstrated for rapid detection of controlled drugs in saliva and urine. See Hao Yu et al, Use of the USDT Flow Immunosensor for Quantitation of Benzolecgonie in Urine, Biosensors and Bioelectronics, 732–734(1996); Nam, D. et al. Programme and Abstracts of TIAFT 2000 at Helsinki, 2000; Liang, G. et al., Proc. of ICADTS 2000, Jun. 22–26, 2000. U.S. Pat. No. 5,183,740 and the above cited references, including any figures contained therein, are hereby incorporated by reference as if fully set forth herein.

To detect $\Delta^9$-THC using an immunoassay or immunosensor, a tracer molecule is usually used to compete with $\Delta^9$-THC or its metabolites. The tracer molecule is usually a labeled antigen or ligand, capable of binding to the same antigen or ligand binding site(s) of an antibody or receptor to $\Delta^9$-THC or its metabolites. In detecting controlled substances, most immunoassays have generally used the labeled illicit drugs themselves, (e.g., labeled $\Delta^9$-THC) as tracers to detect the presence and/or to quantify the analytes in the sample.

Recent use of non-controlled substances as starting materials in $\Delta^9$-THC tracers synthesis has also been reported by Wang, et al, in U.S. Pat. No. 5,264,373 entitled Fluorescence polarization Immunoassay for tetrahydrocannabinoids. In this patent, Wang discloses the use of fluorescein to label THC-analog based derivatives for use in a fluorescence polarization immunoassay.

FIG. 1 generally depicts the various methods for synthesizing tracers used in the detection of $\Delta^9$-THC or it metabolites. Panel A, for example, depicts one of the common methods that use controlled substances, such as the illicit drug, 9-carboxy (or aldehyde)-$\Delta^9$-THC, as starting materials. These starting materials are coupled with labels at the carboxyl group attached to the carbon at position 9 on $\Delta^9$-THC to yield a drug-based tracers. Panel B depicts an alternative method of synthesizing a tracer, which uses $\Delta^9$-THC-analogs.

In certain immunoassay systems such as a continuous flow displacement assay, it is desirable that the binding affinity of the antibody to the tracer molecules be lower than the binding affinity of the antibody to the analyte to facilitate effective displacement. Using a $\Delta^9$-THC-based or $\Delta^9$-THC-analog based tracers is problematic because the $\Delta^9$-THC analyte does not effectively displace the $\Delta^9$-THC -based or $\Delta^9$-THC -analog based tracer. This results in a lower sensitivity of the assay.

Hence, there exists a need for novel reagents, in particular, novel tracers for use in detecting $\Delta^9$-THC.

SUMMARY OF THE INVENTION

The present invention provides a novel set of tracers produced from coupling cannabinol (6,6,9-trimethyl-3-pentyl-6H-dibenzo[b,d]pyran-1-ol) with a label to yield cannabinol-based tracers. In one aspect of the invention, the label can be attached at positions 1, 2, 3, 4, 8, 9, and 10 of the cannabinol molecule.

In another aspect of the invention, the cannabinol-based tracer can be used in conjunction with recognition molecules that are capable of binding to cannabinoids such as $\Delta^9$-THC or its metabolites. Examples of these recognition molecules include antibody or receptor molecules that are capable of binding cannabinoids.

In a preferred embodiment of the invention, the cannabinol-based tracers are used in conjunction with a continuous flow displacement assay system. In this embodiment, it is preferred that the antibody or receptor molecule binds to the cannabinol-based tracer at a lower binding affinity than the affinity to the cannabinoids (e.g., $\Delta^9$-THC or its metabolites) present in the sample.

BRIEF DESCRIPTION OF THE DRAWINGS

FIG. 1 depicts the conventional methods for preparing tracers for THC immunoassay. Method A involves the use of 9-carboxy-$\Delta^9$-THC as a starting material to yield a $\Delta^9$-THC-based tracer. Method B involves the use of non-controlled substances to yield a $\Delta^9$-THC analog-based tracer.

FIG. 10 depicts a cannabinol-based tracer in which a label is attached at position nine according to one embodiment of the present invention.

FIGS. 11 and 12 depict conventional $\Delta^9$-THC-based tracers.

FIG. 13 show the comparison of the flow immunoassay of $\Delta^9$-THC with the preferred tracer GW6–25 from FIG. 11 and the conventional tracers GW5–51, GW2–82 from FIGS. 11 and 12.

FIG. 14 depicts the three dimensional structures of $\Delta^9$-THC, $\Delta^9$-THC analogs, and cannabinol.

DETAILED DESCRIPTION OF THE PREFERRED EMBODIMENTS

Figure 2A:
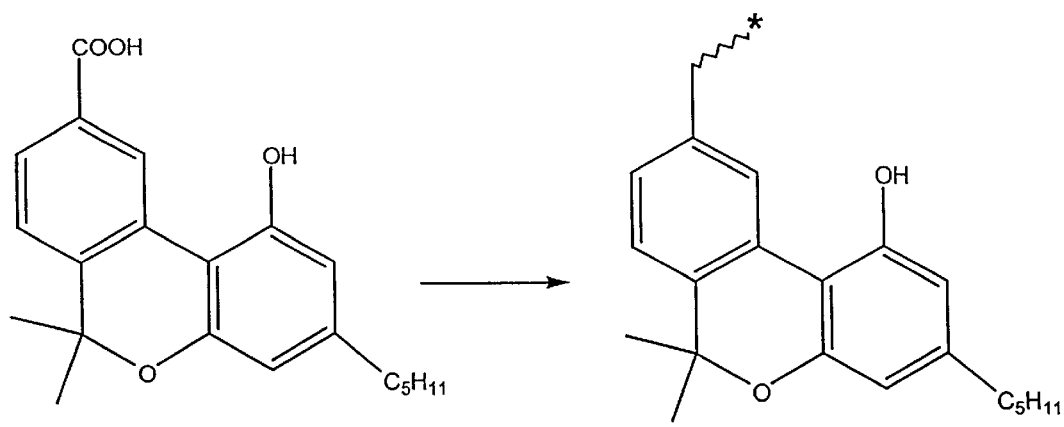
FIG. 2A depicts a general method for synthesizing a cannabinol-based tracer according to one embodiment of the present invention.
Figure 2B:
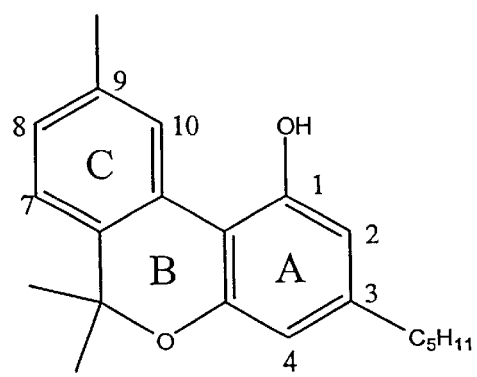
FIG. 2B depicts the chemical formula for cannabinol.

FIG. 2A depicts an example of the general scheme for synthesizing tracers according to one embodiment of the present invention. Instead of using $\Delta^9$-THC or $\Delta^9$-THC -based analog, the tracers are synthesized from cannabinol. Although FIG. 2B depicts the label being attached to the carbon attached to position nine of cannabinol, the label may also be attached at various positions on the cannabinol molecule such as positions 1, 2, 3, 4, 8, 9, and 10 (FIG. 2B). Examples of cannabinol-based tracers labeled at various positions are shown in FIGS. 3–7 and in FIG. 10.

As used herein, cannabinol is defined as 6,6,9-trimethyl-3-pentyl-6H-dibenzo[b,d]pyran-l-ol just as in the Merck index. As shown in FIG. 2B, cannabinol includes two benzene rings A and C with a pyran molecule B in between. Cannabinol derivatives as used herein are defined as molecules that are derived from cannabinol and retain both benzene rings A and C. For example, a 9-carboxyl cannabinol as shown in FIG. 2A will be considered a cannabinol derivative. As used herein, a cannabinol-based tracer is tracer molecule that comprises a label coupled or attached to a cannabinol molecule or a cannabinol derivative. The label may be directly or indirectly (through a linking group) coupled or attached to the cannabinol.

Figure 3:
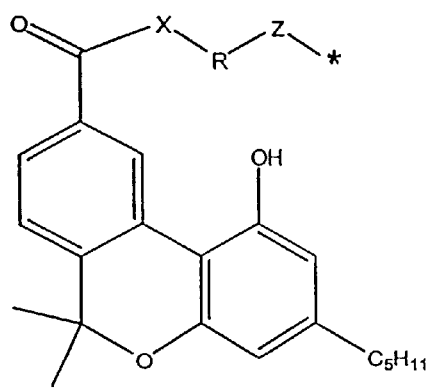
FIG. 3 depicts a cannabinol-based tracer in which a label is attached at position nine according to one embodiment of the present invention.
Figure 4:
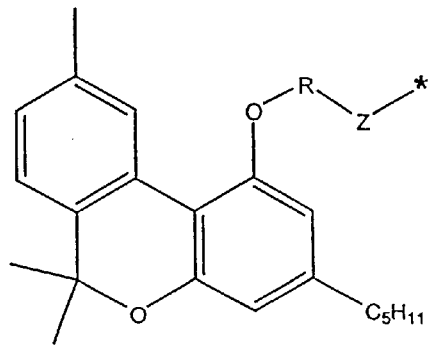
FIG. 4 depicts a cannabinol-based tracer in which a label is attached at position one according to one embodiment of the present invention.

FIGS. 3 and 10 depict cannabinol-based tracers with the label (* or Cy5) attached at position 9 of the cannabinol molecule. FIG. 4 depicts a cannabinol-based tracer with the label (*) attached at position 1 of the cannabinol molecule.

Figure 5:
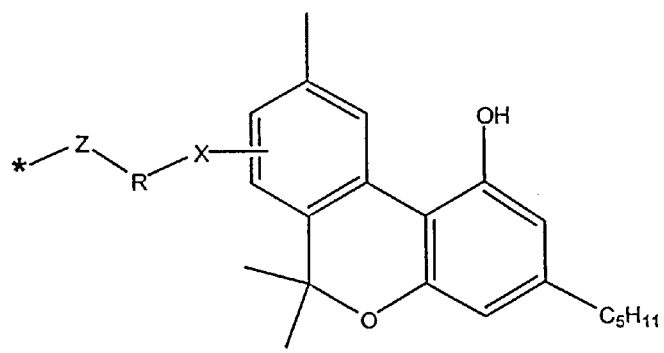
FIG. 5 is a representation of cannabinol-based tracers in which labels are attached on the 8 or 10 position of cannabinol according to one embodiment of the present invention.
Figure 6:
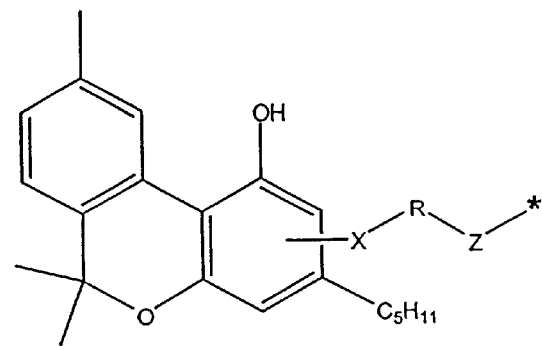
FIG. 6 is a representation of cannabinol-based tracers in which labels are attached on the 2 or 4 position of cannabinol according to one embodiment of the present invention.
Figure 7:
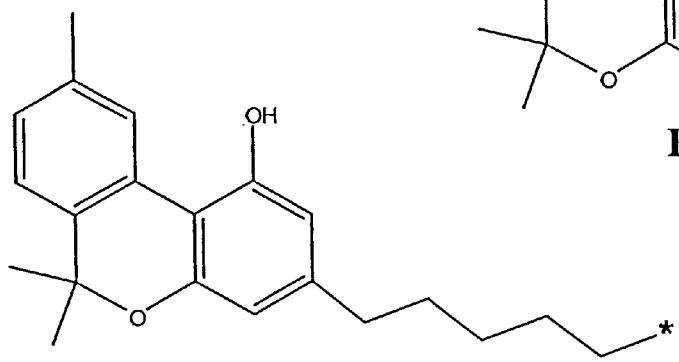
FIG. 7 depicts a cannabinol-based tracer in which a label is attached at position 3 through the pentyl side chain on cannabinol according to one embodiment of the present invention.
Figure 8:
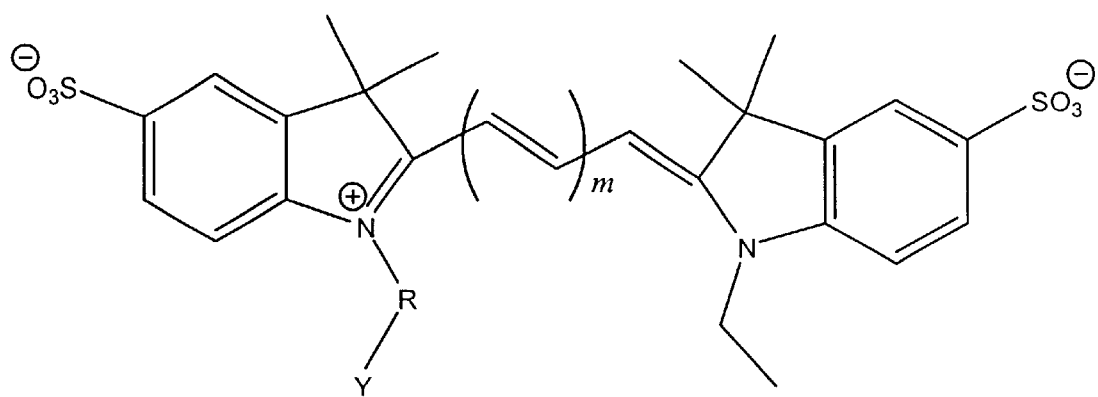
FIGS. 8 and 9 depict examples of common fluorescent labels that may be used in synthesizing the tracer of the present invention.

FIG. 5 depicts a general formula representing a label attached to either position 8 or 10 of the cannabinol molecule. FIG. 6 depicts a general formula representing a label attached to position 2 or 4 of the cannabinol molecule. FIG. 7 depicts the label attached to position 3 of the cannabinol molecule, i.e., at the end carbon of the 3-pentyl chain. The label may also be attached at position 3 via any of the five carbons on the pentyl chain attached at position 3 of cannabinol.

In these figures, X and Z may represent reactive groups such as O, NH, CO, HNCSNH, $CH_2$, S, and $SO_2$. Other examples of X and Z include an imino, an iminocarbonyl, a carbonyl, a carbonimidoyl, an iminosulfonyl, a sulfonyl, an iminocarbonimidoyl, a thiocarbonyldiimino, an iminocarbonyloxy, an iminothiocarbonyloxy, a (sulfonyliminocarbonyl)diimino, a triazinyldiimino, ethylene diamine (EDA) or a succinimidyl active ester (OSu) group. R may represent an extending group, i.e., a group of atoms that further extend the label (*) away from the cannabinol molecule. Examples of R may include a group of about zero to about 15 carbon atoms bonded with heteroatoms such as N, O, S, Cl, Br, I, or F. Specific examples of R include —$(CH_2)n$— and $C(O)$—$(CH_2)nCO$; wherein n maybe from about zero to about 15.

The use of cannabinol-based tracers may increase the sensitivity of an immunoassay, in particular, when used in a displacement-based immunoassay as will be demonstrated in Example VII, in conjunction with FIG. 13. Structurally, cannabinol differs from $\Delta^9$-THC in that cannabinol has two benzene rings A and B (see FIGS. 2B and 14) in contrast with $\Delta^9$-THC or $\Delta^9$-THC analog that has only one benzene ring (A' in FIG. 14). As such, the three dimensional structure of cannabinol is significantly different than $\Delta^9$-THC or $\Delta^9$-THC analogs. FIG. 14 provides a representation of the three-dimensional structures of cannabinol, $\Delta^9$-THC, and $\Delta^9$-THC -analogs.

Because of the two benzene rings A and C on both sides of the pyran molecule B in cannabinol, its three-dimensional structure may be characterized as a single and almost flat plane. The plane consists of the two benzene rings A and C and the pyran molecule B. (See FIG. 14). In contrast, the three-dimensional structure of $\Delta^9$-THC or $\Delta^9$-THC -analogs may be characterized by a molecule having two planes, wherein the rings B' and C' are in a typical chair conformation. (FIG. 14). The first plane consists of the benzene ring A' and part of the pyran molecule (B). The second plane consists of the cyclohexene or six membered carbon molecule C', which forms a typical chair configuration in three dimension. The pyran molecule B' also forms a typical chair configuration in three dimensions. Because of the difference in the three-dimensional structure of cannabinol and $\Delta^9$-THC or $\Delta^9$-THC analogs, antibody that binds to $\Delta^9$-THC cross-reacts with cannabinol but at a lower binding affinity. This lower binding affinity is especially desirable because in certain immunoassay such as a displacement based immunoassay, the cannabinol-based tracers are easier to displace by $\Delta^9$-THC, thereby resulting in greater sensitivity of the assay.

Thus, one embodiment of the present invention contemplates a tracer molecule that is structurally dissimilar to the analyte molecule and retains sufficient cross-reactivity to an antibody that is capable of binding to $\Delta^9$-THC or its metabolites, but preferably at a lower binding affinity.

In a preferred embodiment of the invention, the cannabinol-based tracers are used in conjunction with a displacement assay to detect cannabinoids such as $\Delta^9$-THC or its metabolites. As used herein, "detect," means to determine the presence or to quantify the amount (or both) of $\Delta^9$-THC or its metabolites (or both) in a sample. In a displacement immunoassay, the presence or amount of $\Delta^9$-THC or its metabolites may be determined by the amount of labeled tracer molecules that is bound to a recognition molecule and that the $\Delta^9$-THC or its metabolites may displace from the recognition molecule. Examples of recognition molecules include antibodies or receptor molecules (such as the cannabinoid receptors) that recognize $\Delta^9$-THC or its metabolites. These recognition molecules may be first immobilized in a solid phase-matrix or a solid support using conventional means. The solid support or solid-phase matrix may be a resin, a bead, a microsphere, wall of a column, or a microtiter plate. Examples of the resin, bead, or microsphere include sepharose, sephacryl, silica, Emphase porous beads, Dynal beads, paramagnetic beads and any other types of reactive resin or beads. Once immobilized to the solid support or solid-phase matrix, the recognition molecules can be exposed to the tracer molecules for binding either in a column or batch format. Preferably, the tracer molecules are incubated with the recognition molecules at high concentrations such that the tracer molecules bind and saturate all of the ligand binding sites on the recognition molecule.

Afterwards, a sample suspected of having $\Delta^9$-THC or its metabolites may be incubated with (batch format) or flowed past (column or continuous flow format) the recognition molecule-tracer complex such that the $\Delta^9$-THC or its metabolites in the sample displaces the labeled tracer from the complex. The amount of labeled tracer may then be measured and, the amount of which is directly proportional to the THC or its metabolites in the sample.

As alluded above, it is not necessary to have the target molecule or analyte (e.g. $\Delta^9$-THC or its metabolites) itself as the binding site of the prepared tracer as long as the binding site in the prepared tracer has a lower cross-reactivity for the selected recognition molecule than the analyte in the test sample. As will described in further detail below, cannabinol-based tracers are ideal for use in immunoassays that detect the presence and/or quantify cannabinoids in biological samples. They are also particularly useful in a continuous flow displacement immunoassay.

Continuous Flow Displacement Immunoassay

In a continuous flow displacement immunoassay, the kinetic properties of the analyte and the antibody play a very important role. An analyte is the substance being tested in an immunoassay; for instance, the analyte can be $\Delta^9$-THC or its metabolites. The antibody recognizes or is capable of specifically binding to the analyte. To allow for determination of the presence of the analyte, a tracer, which is a labeled compound, is allowed to compete with the analyte for binding to the antibody.

A typical continuous flow displacement immunoassay involves a solid-phase immobilized antibody to $\Delta^9$-THC or its metabolites. The antigen binding site of the antibody may be exposed to a synthetic labeled tracer to form a labeled synthetic tracer-antibody complex. The antibody may be exposed to tracers such that the antigen binding sites of the antibody are saturated with the labeled synthetic tracers. Next, a biological sample suspected of containing the analyte, $\Delta^9$-THC, may be continuously flowed past the solid-phase immobilized antibody-labeled synthetic tracer complex. If the analyte is present in the sample, the analyte may bind to the antibody and displace the labeled synthetic tracer. Detection of the labeled tracer downstream from the binding point may thus show the presence and/or quantity of the analyte present in the biological sample. See Ligler, et al., U.S. Pat. No. 5,183,740, which is incorporated by reference as if fully set forth herein.

The success of developing a continuous flow displacement immunoassay is based on the selection of antibody and tracer to achieve a fast dissociation rate of the bound tracer from the antibody, thereby permitting a rapid binding of the analyte. In general, the ideal continuous flow displacement immunoassay utilizes a system where the antibody has a high affinity for the analyte, and a lower affinity for the tracer. The affinity of the antibody for the tracer may be anywhere between 15–100% cross-reactivity. A preferred cannabinol-based tracer has about 40–80% cross-reactivity for the antibody as will be described in Example VII. In addition, the condition for displacing a tracer from the recognition molecule is preferably carried out in non-equilibrium condition or kinetic flow reaction. By "non-equilibrium condition or kinetic flow reaction," it is meant that the sample flows past the recognition molecule-tracer complex at a rate where a stable equilibrium state between the recognition molecule, tracer, and analyte has not been achieved.

Since most antibodies to $\Delta^9$-THC also recognize the important metabolites of $\Delta^9$-THC such as $\Delta^9$-THC-9-carboxy, the cannabinol-based tracers are also useful so long as the antibodies are capable of recognizing the $\Delta^9$-THC analogs.

Antibodies

Any antibodies, such as monoclonal or polyclonal antibodies, directed toward $\Delta^9$-THC or $\Delta^9$-THC -metabolites may be employed or adapted to the methods described in this disclosure for identifying a wide range of $\Delta^9$-THC or $\Delta^9$-THC—metabolites. An example of the antibody can be obtained from Fitzgerald Industries International, Inc. (Concord, Mass.) catalog #10-T43.

Label

Figure 9:
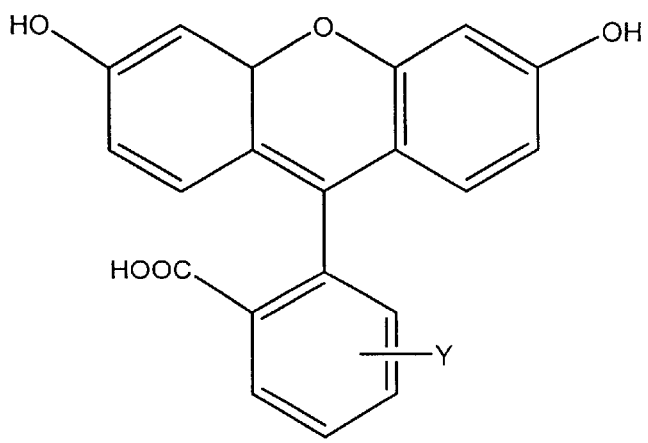

The label for labeling the cannabinol-based tracer may suitably be a fluorophore, a chromophore, a radiolabel, a hapten, a metal colloid, an enzyme, or a chemiluminescent or bioluminescent molecule. Suitable fluorophores and chromophores are disclosed in R. P. Haugland, Molecular Probes, Handbook of Fluorescent Probes and Research Chemicals, 5$^{th}$ Ed., Molecular Probes, Inc., Eugene, Oreg., 1992, which is incorporated herein by reference. Examples of preferred fluorophores include fluorescein, rodamine, and sulformdocyanine dye Cy5 (Mujumdar, R. B., et al., Bioconjugate Chemistry, vol. 4, p. 105 (1992). Other examples of a fluorescent dye are provided in FIGS. 9 and 10.

Examples of a hapten may include biotin, digoxygenin, or any other suitable hapten that may be recognized by an antibody, streptavidin, or any other ligand binding molecule. Examples of enzymes may include alkaline phosphatase, peroxidase, β-galactosidase, or any other enzyme capable of cleaving a reporter molecule to produce color, precipitation, or luminescence.

Linking Group

The label may be coupled to the cannabinol-based tracers usually by means of a linking group. An example of a linking group is illustrated by X–R–Z-* wherein * is the label.

X and Z may represent reactive groups such as O, NH, CO, HNCSNH, CH$_2$, S, and SO$_2$. Other examples of X and Z include an imino, an iminocarbonyl, a carbonyl, a carbonimidoyl, an iminosulfonyl, a sulfonyl, an iminocarbonimidoyl, a thiocarbonyldiimino, an iminocarbonyloxy, an iminothiocarbonyloxy, a (sulfonyliminocarbonyl)diimino, a triazinyldiimino, ethylene diamine (EDA) or a succinimidyl active ester (OSu) group. R may represent an extending group, i.e., a group of atoms that further extend the label (*) away from the cannabinol molecule. Examples of R may include a group of about zero to about 15 carbon atoms bonded with heteroatoms such as N, O, S, Cl, Br, I, or F. Specific examples of R include —($CH_2$)n— and C(O)—($CH_2$)nCO; wherein n maybe from about zero to about 15.

Biological Samples

The cannabinol-based tracers may be used to detect THC or its metabolites in biological or aqueous samples, including but not limited to blood, plasma, serum, hair, saliva or urine. Saliva has been demonstrated as a useful test matrix for the detection and measurement of drugs of abuse. ("Saliva as a Diagnostic Fluid", Ed by D. Malamud and L. Tabak, Annals of the New York Academy of Sciences, 1993, V. 694.) For example, $\Delta^9$-THC in saliva samples can be detected by GC/MS (H. W. Peel et al, Detection of Drugs in Saliva of Impaired Drivers", J. Forensic Sciences, JFSCA, V29, 185(1984).

The following examples illustrate the synthesis and use of cannabinol-based tracers for detecting THC or its metabolites in a biological sample. The chemical starting materials may be purchased from Research Triangle Institute (RTI) (Research Triangle Park, N.C.) or from Sigma Chemicals (St. Louis, Mo.).

EXAMPLE I

Preparation of Cy5 Labeled Tracers Labeled at Position 2 or 4 of Cannabinol

Figure 15:
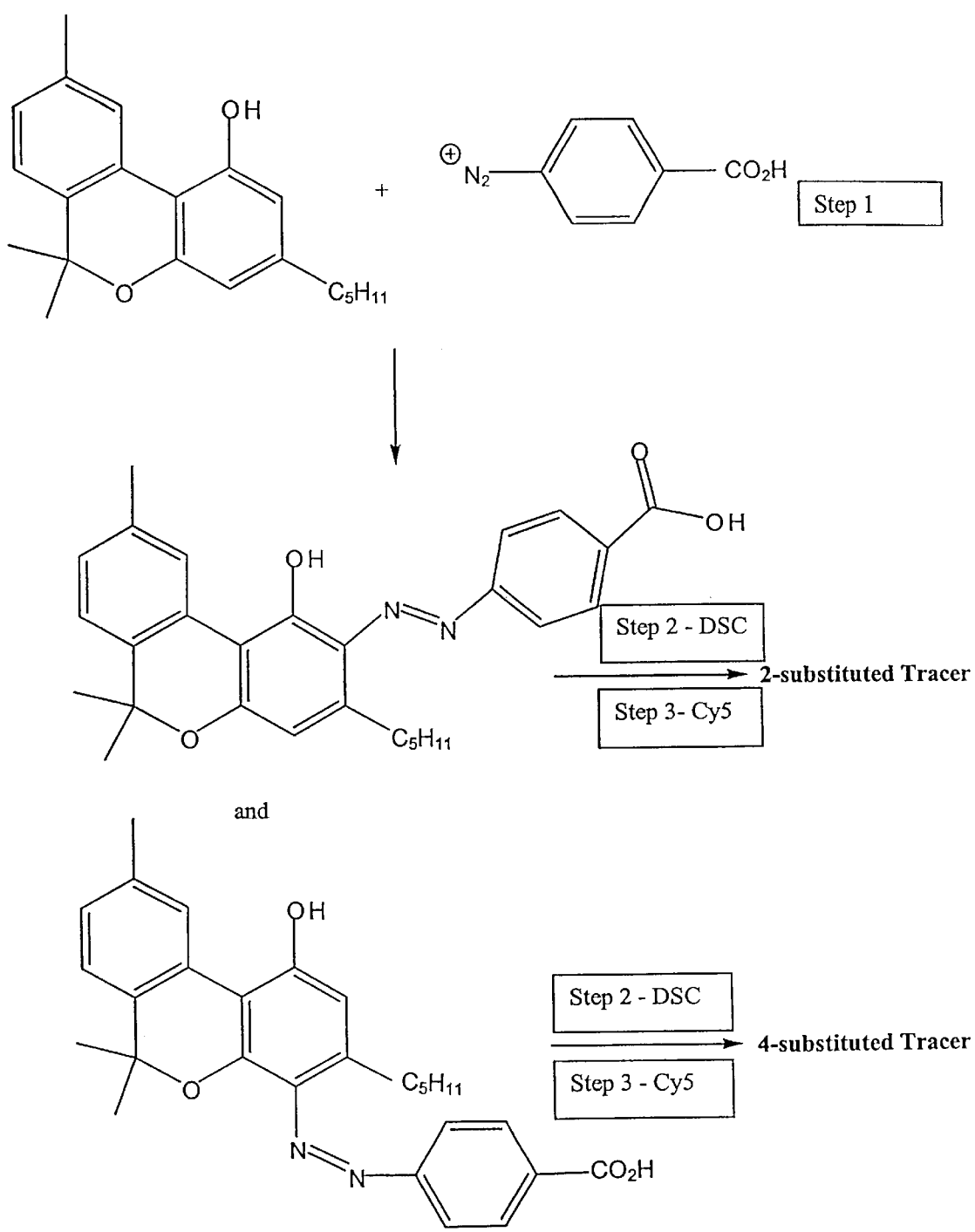
FIG. 15 depicts the process for preparing a cannabinol-based molecule labeled at position 2 or 4.

FIG. 15 depicts the process of preparing Cy5 labeled tracers at position 2 or 4 of cannabinol. In step one, cannabinol (25 mg) was dissolved in 0.2N NaOH (1 mL) and reacted with p-carboxybenzyldiazonium salt at room temperature (RT) for 30 min. The resulting dark yellow solution was adjusted with 1N HCl to pH 3, and the reaction product was extracted with EtOAc and dried over $Na_2SO_4$. The drying agent present in the residue was filtered off and dried under decreased pressure. The dried residue was then redissolved in THF (0.5 mL) and purified using thin layer chromatography with a silica plate (20×20 cm, 1000 $\mu$M) developed with EtOAc/Hexane (1:1). Using the above synthesis method, about 11 mg of 2-substituted and 6 mg of 4-substituted cannabinol derivatives were obtained, respectively, the chemical structures of which are depicted in FIG. 15.

In step two, the resulting 4-substituted cannabinol derivative (6 mg) was reacted with N,N'-disuccinimidyl carbonate (DSC, 8 mg) in the presence of pyridine (20 mg) and acetonitrile (2 mL) at refluxing conditions for 6 hour. The resulting succinimidyl active ester of cannabinol (4 mg) was the added in step three to Cy5EDA solution in 1 mL of PBS buffer (pH 9) at RT. The resulting mixture was stirred at RT for 4 hours, and then the mixture was directly spotted on a C18 plate (20×20 cm, 1000 $\mu$m), and developed with methanol and water in a ratio of 70/30(v/v). The product band was cut and extracted with methanol. The resulting tracer solution, containing a Cy5-labeled cannabinol at position 4, can be directly used in an immunoassay.

Using the same procedure for the 4-substituted cannabinol derivative, cannabinol-based tracer labeled at position 2 of cannabinol may also be achieved using the 2-substituted cannabinol derivative as starting material in step two. The resulting cannabinol-based tracer with a label attached to position 2 or 4 as produced by the above preparation method may have a general formula as shown in FIG. 5.

EXAMPLE II

Preparation of Preferred Tracer GW2–25 as Shown in FIG. 11

Preferred tracer GW2–25, which is a tracer having a label attached to position 9 of the cannabinol molecule was sysnthesized as follows: The succinimidyl active ester of cannabinol-9-carboxy (1 mg) (from Research Triangle Institute) was added to a solution of Cy5EDA (3 mg) in 1 mL of PBS buffer (pH=9) at room temperature (RT). The resulting mixture was stirred at RT for 4 hours, and then the mixture was directly spotted on a C18 plate (20×20 cm, 1000 $\mu$m), and developed with methanol and water in a ratio of 70/30(v/v). The product band was cut and extracted with methanol. The resulting tracer, as shown in FIG. 11 as GW6–25, may be directly used in an immunoassay.

EXAMPLE III

Preparation of Cannabinol-Based Tracers Labeled at Position 8 or 10

Cannabinol-based tracers with label attached to position 8 or 10 of the cannabinol molecule may be synthesized by reacting 8 or 10-oxygenated cannabinol with Cy5Osu to obtain 8 or 10-Cy5-labeled cannabinol-based tracers. 8 or 10-oxygenated cannabinol may be synthesized according to the methods described in Novak, J. et al., J. Chem. Soc. Perkin. Trans. 12867 (1983), which is hereby incorporated by reference as if fully set forth herein.

EXAMPLE IV

Preparation of Cannabinol Based Tracers with Label at Position 3

Functionalized pentyl chain at position 3 of the cannabinol molecule may be synthesized using the methods described in Singer, M et al, Synthesis, May 1994, p486–488, which is hereby incorporated by reference as if fully set forth herein. The functional group attached to the pentyl chain may be a carbonyl or carboxyl group and may be attached at any carbon atoms on the pentyl chain. The carbonyl or carboxyl group may then be reacted with Cy5-EDA in the presence of 1,3-dicyclohexylcarbodiimied to yield a cannabinol-based tracer labeled at position 3.

EAMPLE V

Preparation of Cannabinol Based Tracers with Label at Position 1

To obtain a cannabinol-based tracer labeled at position 1, cannabinol may be reacted with $BrCH_2COOH$ in the presence of $K_2CO_3$ to obtain a cannabinol derivative with O—$CH_2COOH$ attached to the carbon atom at position 1 of cannabinol. The cannabinol derivate having O—$CH_2COOH$ at position 1 may then be reacted with Cy5-EDA in the presence of 1,3-dicyclohexylcarbodiimied to yield a cannabinol-based tracer labeled at position 1.

EXAMPLE VI

Preparation of Conventional Tracers for Used in Comparing with the Cannabinol-Based Tracers The reactive ester, 1 1-[(N-succinimidyl) oxycarboxylmethoxyimino]-delta-8-THC (4 mg), was added to a solution of Cy5EDA (6 mg) in PBS buffer (1 mL, pH=9) at room temperature (RT). The resulting mixture was stirred at RT for 4 hours, and then the mixture was directly spotted on a C18 plate (20×20 cm, 1000 $\mu$m) and developed with methanol and water in a ratio of 70/30(v/v). The product band was cut and extracted with methanol. The resulting tracer is the tracer molecule, GW2–82 shown in FIG. 13.

EXAMPLE VII

Procedure of Continuous Flow Immunoassay of $\Delta^9$-THC a) Continuous Flow Immunoassay Instrument:

A flow immunoassay instrument which contains the necessary pumps, valves, tubing, exchangeable columns and fluorescence detector for performing a continuous flow displacement immunoassay has been disclosed in Liegler et. al., U.S. Pat. No. 5,183,740, which has already been incorporated herein by reference.

THC standards were prepared by adding $\Delta^9$-THC at different concentrations (e.g., 0 ng/mL, 25 ng/mL and 100 ng/mL) into the saliva from a person who has not smoke marijuana. Chemicals and buffers were obtained from Sigma and Aldrich, Company.

b) Preparation of Reagents

To determine the presence of the added $\Delta^9$-THC in saliva, a specific anti-THC monoclonal antibody (available from Fritzgerald Industries, Inc., Concord, Mass., cat.#10-T43) was coupled to or immobilized on Emphase porous beads according to the manufacturer's standard protocol. The antibody-coupled beads were then saturated with prepared Cy5-labeled tracers as shown in FIGS. 10–12. The resulting tracer-antibody-resin complex mixture was left overnight at 4° C. with continuous mixing using a roller mixer. The complex resin was washed with 0.1M PBS (10% MeOH) until a stable baseline was obtained. The washed resin was added to an equal volume of 150 mM trehalose buffer in 50 mM PBS (pH 7.4). The resin was then freeze-dried and stored until ready to use.

c) Flow Assay

A micro-polystyrene column with an inner diameter of 2 mm and a length of 10 mm was filled with 4 mg of the prepared resin. The filled column was installed into one of the flow channels of the flow immunoassay instrument. The column was also pre-washed with an appropriate buffer controlled by an automatic system supported by Labview software (National Instruments, Inc.). Afterwards, 50 µl of the saliva sample spiked with THC was passed through the channel at a flow rate of 100 to 300 µl/minute. The immunoassay profiles are shown in FIG. 13.

FIG. 13 provides an example of the results in comparing the sensitivity of a cannabinol-based tracer (GW6–25) to $\Delta^9$-THC-based tracer (GW5–51, GW2–82, and GW6–10) in a continuous flow displacement assay. When THC containing sample is passed through the column, GW6–25 is effectively displaced from the antibody on the column as seen by the increasing amount of fluorescence that can be detected flowing out of the column. As compared with the $\Delta^9$-THC-based tracers, GW6–25 provides the highest sensitivity in detecting $\Delta^9$-THC at $\Delta^9$-THC concentrations of 25 ng/mL, and 100 ng/mL. Using the cannabinol-based tracer GW6–25 results in about 2 to about 20 fold increase in sensitivity at 100 ng/mL of THC and about 1.5 to about 8 fold increase in sensitivity at 25 ng/mL of $\Delta^9$-THC.

EXAMPLE VIII

The lower binding affinity of an antibody to a particular tracer may be measured by the percent cross-reactivity of the antibody to the tracer as compared to the analyte in a sample. For example, immobilized antibodies against $\Delta^9$-THC were bound with the cannabinol-based tracer (shown in FIG. 10) similar to the methods as described in Example VII. Different samples containing 25 ng/mL of $\Delta^9$-THC (unlabeled), $\Delta^8$-THC (unlabeled), unlabeled 9-carboxy-$\Delta^9$-THC (THCA), cannabidiol (unlabeled), or unlabeled cannabinol were flowed through different columns having the antibody-tracer complex to determine the amount of cross-reactivity. The amount of tracer displaced was then compared between the different samples.

The results are summarized in Table 1 below:

TABLE I

| MAX FI (mV) | $\Delta^9$-THC | $\Delta^8$-THC | Cannabidiol | Cannabinol | THCA |
|---|---|---|---|---|---|
| 0 | 422 | 422 | 422 | 422 | 422 |
| 25 ng/mL | 1602 | 1488 | 624 | 1266 | 8700 |

Using $\Delta^9$-THC as the standard (i.e., $\Delta^9$-THC set at 100% cross-reactivity) (1602/1602)), 9-carboxy-$\Delta^9$-THC has a percent cross-reactivity of about 540% (8700/1602), and cannabinol has a percent cross-reactivity of about 79% (1266/1602). If 9-carboxy-$\Delta^9$-THC were used as the standard (i.e., 9-carboxy-$\Delta^9$-THC set at 100% cross-reactivity (8700/8700)), then the percent cross-reactivity for cannabinol would be about 14.5% (1266/8700). If $\Delta^8$-THC were used as a standard (i.e., $\Delta^8$-THC set at 100% cross-reactivity (1488/1488)), then the present cross-reactivity for cannabinol would be about 85% (1266/1488).

Although the present invention has been described above in the context of certain preferred embodiments, one skilled in the art would understand that various modifications may be made to those embodiments and various equivalents may be substituted without departing from the spirit or scope of the invention. In addition, the above examples are provided for illustration purposes only and are not intended to limit the invention.

What is claimed is:

1. An immunoassay system for detecting tetrahydrocannabinoids in a sample, the system comprising:
   (a) a tracer molecule comprising
       a cannabinol molecule or a derivative of cannabinol molecules, wherein the derivative comprises at least two benzene rings of the cannabinol molecule;
       a label coupled to the cannabinol molecule or the derivative of cannabinol molecules;
   (b) a recognition molecule having a binding site that is capable tetrahydrocannabinoids and to the tracer, and
   (c) wherein the immunoassay is configured such that the tetrahydrocannabinoids in the sample competes with the tracer for binding site on the recognition molecule.

2. The immunoassay system of claim 1 wherein the recognition molecule is bound to the tracer and the tetrahydrocannabinoid competes with the tracer by displacing the tracer from the recognition molecule.

3. The immunoassay system of claim 1 wherein the recognition molecule is selected from the group consisting of an antibody, a receptor for $\Delta^9$-THC, and a receptor for $\Delta^9$-THC metabolites.

4. The immunoassay of claim 2 wherein the immunoassay is configured as a kinetic displacement assay.

5. The immunoassay of claim 2 wherein the antibody is immobilized on a solid support.

6. The immunoassay system of claim 2 wherein the antibody has a lesser binding affinity to the tracer than to the tetrahydrocannabinoid.

7. The immunoassay system of claim 6 wherein the tracer has about 14% to about 85% cross-reactivity to the antibody as compared to the tetrahydrocannabinoid.

8. The immunoassay system of claim 1 wherein the label is coupled to the cannabinol molecule or its derivatives at positions selected from the group consisting of positions 1, 2, 3, 4, 8, 9, and 10.

9. The immunoassay of claim 1 wherein the label is selected from the group consisting of: a fluorophore, a chromophore, a hapten, a radiolabel, a metal colloid, an enzyme, a chemiluminescent molecule, and a bioluminescent molecule.

10. The immunoassay system of claim 1 further comprising a sensor for detecting the label coupled to the cannabinol molecule or to the derivative of cannabinol molecules.

11. The immunoassay of claim 9 wherein the fluorophore is selected from the group consisting of:

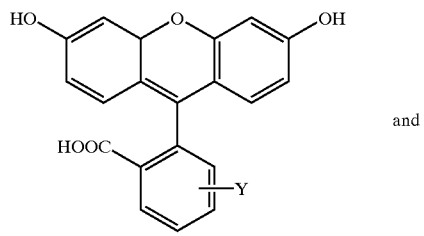

and

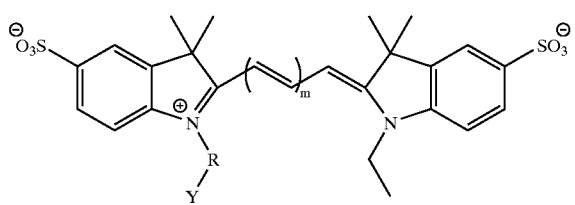

wherein:
(a) m is a number selected from the group consisting of 0, 1, 2, 3, and 4; and
(b) Y is a compound selected from the group consisting of a succimidyl active ester (OSu) and an ethylene diamine (EDA).

12. The immunoassay system of claim 8 wherein the tracer has a general formula selected from the group consisting of:

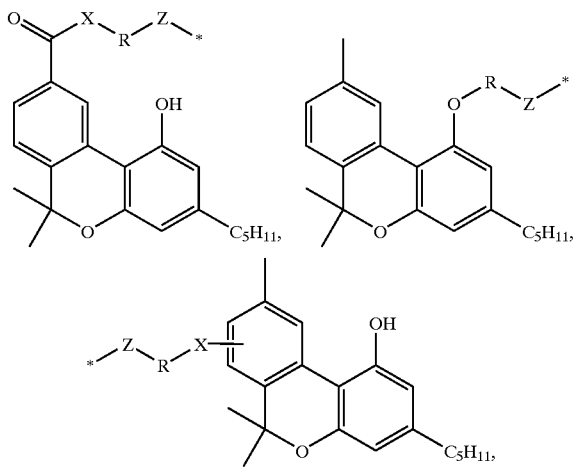

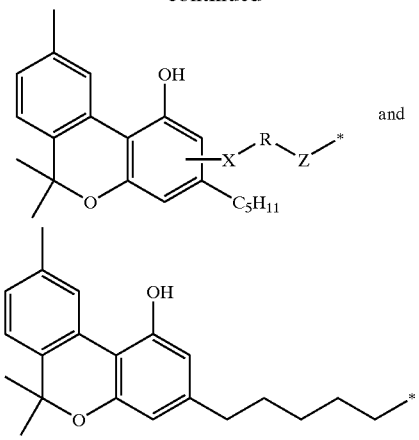

wherein:
(a) R is an extending group;
(b) X and Z are reactive groups; and
(c) * is the label.

13. The immunoassay system of claim 12 wherein R is selected from the group consisting of —(CH$_2$)n— and C(O)—(CH$_2$)nCO; wherein n may be from about zero to about 15.

14. The immunoassay system of claim 12 wherein X or Z, or both, are selected from the group consisting of an imino, an iminocarbonyl, a carbonyl, a carbonimidoyl, an iminosulfonyl, a sulfonyl, an iminocarbonimidoyl, a thiocarbonyldiimino, an irninocarbonyloxy, an iminothiocarbonyloxy, a (sulfonyliminocarbonyl)diimino, a triazinyldiimino, ethylene diamine (EDA) or a succinimidyl active ester (OSu) group.

15. The immunoassay system of claim 8, wherein the label is coupled at position 9 of the cannabinol and the tracer has the general formula:

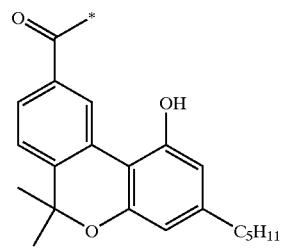

and wherein * is the label.

16. The immunoassay system of claim 15 wherein the label is EDA-Cy5.

17. A method for detecting tetrahydrocannabinoids in a sample, the method comprising the steps of:
(a) exposing a recognition molecule to a synthetic tracer to form a recognition molecule-tracer complex, wherein the tracer comprises
 a cannabinol molecule or a derivative of cannabinol molecules, wherein the derivative comprises at least two benzene rings of the cannabinol molecule;
 a label coupled to the cannabinol molecule or the derivative of cannabinol molecules;
(b) contacting a sample suspected of containing tetrahydrocannabinoids with the recognition molecule-tracer complex such that the tetrahydrocannabinoids displace the tracer from the recognition molecule; and
(c) detecting the tracer that is displaced.

18. The method of claim 17 wherein the recognition molecule is immobilized on a solid support.

19. The method of claim 18 wherein the step of contacting the sample with the recognition molecule-tracer complex further comprises the step of continuously flowing the sample past the recognition molecule-tracer complex under non-equilibrium conditions.

20. The method of claim 18 wherein the step of exposing the recognition molecule with the tracer saturates binding sites on the recognition molecule with the tracer.

21. The method of claim 18 wherein the amount of displaced tracer is directly proportional to the concentration of $\Delta_9$-THC and its metabolites in the sample.

22. The method of claim 18 wherein the label is coupled to the cannabinol molecule or derivatives thereof at a position selected from the group consisting of positions 1, 2, 3, 4, 5, 8, 9, and 10.

23. The method of claim 22 wherein the tracer has a general formula selected from the group consisting of:

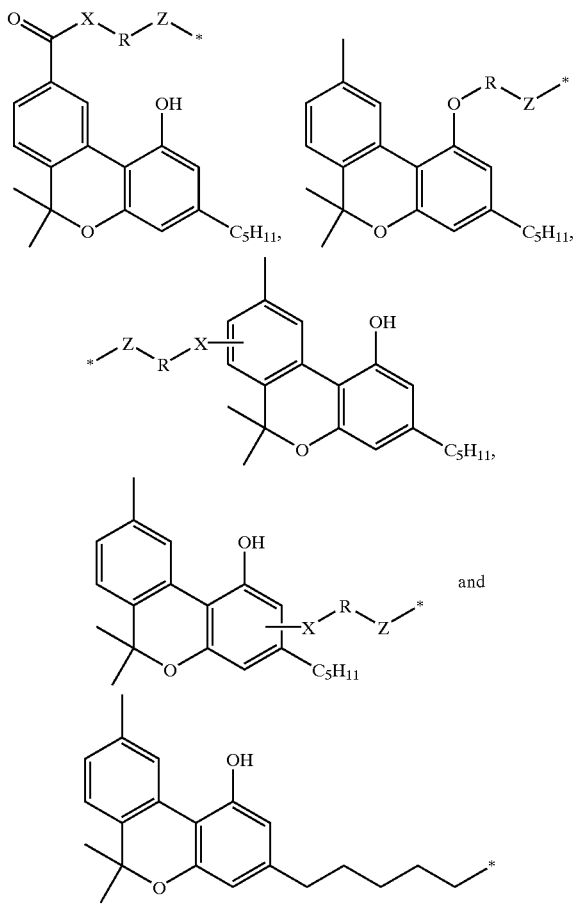

and wherein R is an extending group, X and Z are reactive groups and * is a label.

24. The method of claim 23 wherein R is selected from the group consisting of —(CH$_2$)n— and C(O)—(CH$_2$)nCO; wherein n may be from about zero to about 15.

25. The method of claim 23 wherein X or Z, or both, are selected from the group consisting of an imino, an iminocarbonyl, a carbonyl, a carbonimidoyl, an iminosulfonyl, a sulfonyl, an iminocarbonimidoyl, a thiocarbonyldiimino, an iminocarbonyloxy, an iminothiocarbonyloxy, a (sulfonyliminocarbonyl)diimino, a triazinyldilmino, ethylene diamine (EDA) or a succinimidyl active ester (OSu) group.

26. The method of claim 17, wherein the label is coupled to the cannabinol at position 9 and the tracer has a formula:

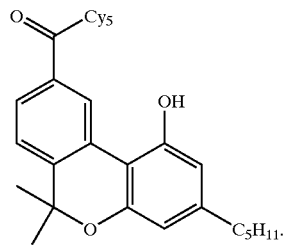

27. The method of claim 17 wherein the sample is a biological sample selected from the group consisting of saliva, whole blood, serum, plasma, hair, or urine.

28. The method of claim 17 wherein the sample is an aqueous sample.

29. The method of claim 17 wherein the recognition molecule is selected from the group consisting of an antibody, a receptor that binds to $\Delta_9$-THC, and a receptor that binds to $\Delta_9$-THC metabolites.

30. A column comprising:
   a solid support;
   an antibody immobilized to the solid support, wherein the antibody is capable of binding to tetrahydrocannabinoids;
   a tracer molecule bound to the antibody, wherein the tracer molecule comprises:
      a cannabinol molecule or a derivative of cannabinol molecules, wherein the derivative comprises at least two benzene rings of the cannabinol molecule; and
      a label coupled to the cannabinol molecule or the derivative of cannabinol molecules.

31. The column in claim 30 wherein the solid support is selected from the group consisting of a resin, a bead, and a wall of the column.

32. The column in claim 30 wherein the antibody is capable of binding to $\Delta_9$-THC or its metabolites.

33. A method of using a synthetic tracer to detect tetrahydrocannabinoids in a sample comprising the steps of:
   (a) collecting a sample suspected of containing tetrahydrocannabinoids;
   (b) exposing the sample and a synthetic tracer to a recognition molecule, wherein the tracer comprises a cannabinol molecule or a derivative of cannabinol molecules, wherein the derivative comprises at least two benzene rings of the cannabinol molecule, and a label coupled to the cannabinol molecule or the derivative of cannabinol molecules, and wherein the tracer competes with the tetrahydrocannabinoids for binding on the recognition molecule;
   (c) measuring the amount of label that is coupled to the synthetic tracer that has been displaced from the recognition molecule.

34. The method of claim 33 further comprising the step of mixing the synthetic tracer with the sample before exposing the sample and synthetic tracer to the recognition molecule.

35. The method of claim 34 wherein the step of measuring the label comprises measuring the label from synthetic tracers that is not bound to the recognition molecule.

36. The method of claim 33 wherein the exposing step comprises first exposing the synthetic tracer to the recognition molecule to form a recognition molecule-tracer complex and then exposing the sample to the recognition molecule-tracer complex.

37. The method of claim 36 wherein the step of exposing the synthetic tracer to the recognition molecule saturates binding sites on the recognition molecules with the synthetic tracer.

38. The method of claim 36 wherein the step of exposing the sample to the recognition molecule-tracer complex further comprises the step of continuously flowing the sample past the recognition molecule-tracer complex under non-equilibrium conditions.

39. The method of claim 33 wherein the amount of displaced synthetic tracer is directly proportional to the concentration of $\Delta_9$-THC and its metabolites in the sample.

40. The method of claim 33 wherein the recognition molecule is immobilized on a solid support.

41. The method of claim 33 wherein the label is coupled to the cannabinol molecule or its derivatives at a position selected from the group of positions 1, 2, 3, 4, 5, 8, 9, and 10.

42. The method of claim 33 wherein the synthetic tracer has a general formula selected from the group consisting of:

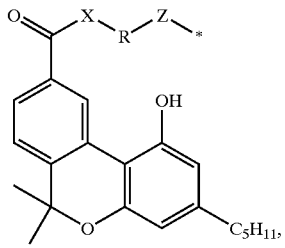,
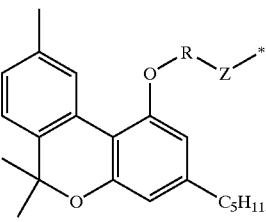,

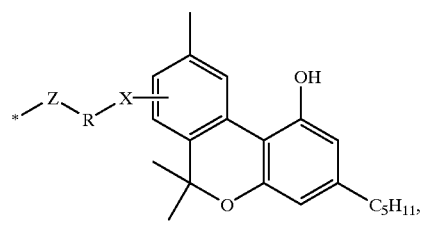,

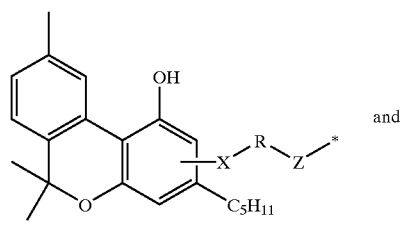

and

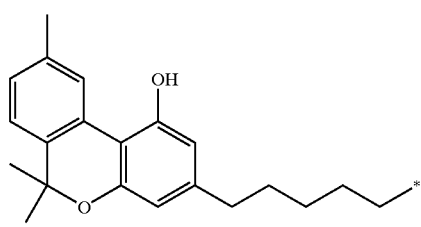

wherein
(a) R is an extending group,
(b) X and Z are reactive groups, and
(c) * is a label.

43. The method of claim 33 wherein R is selected from the group consisting of—$(CH_2)n$— and $C(O)$—$(CH_2)nCO$ and wherein n may be from about zero to about 15.

44. The method of claim 33 wherein X or Z, or both, are selected from the group consisting of an imino, an iminocarbonyl, a carbonyl, a carbonimidoyl, an iminosulfonyl, a sulfonyl, an iminocarbonimidoyl, a thiocarbonyldiimino, an iminocarbonyloxy, an iminothiocarbonyloxy, a (sulfonyliminocarbonyl)diimino, a triazinyldilmino, ethylene diamine (EDA) or a succinimidyl active ester (OSu) group.

45. The method of claim 33 wherein the label is coupled to the cannabinol at position 9 and the synthetic tracer has a general formula:

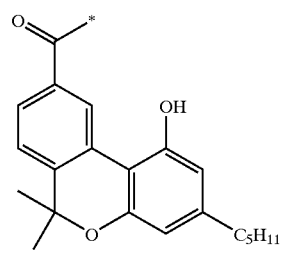

and wherein * is a label.

46. The method of claim 33 wherein the sample is a biological sample selected from the group consisting of saliva, whole blood, serum, plasma, hair, or urine.

47. The method of claim 33 wherein the sample is an aqueous sample.

48. The method of claim 33 wherein the recognition molecule is selected from the group consisting of an antibody, a receptor that binds to $\Delta^9$-THC, and a receptor that binds to $\Delta^9$-THC metabolites.

49. A method of using a synthetic tracer to detect tetrahydrocannabinoids comprising the steps of:
attaching a recognition molecule to a solid support, wherein the recognition molecule is capable of binding to tetrahydrocannabinoids;
exposing a synthetic tracer to the recognition molecule, wherein the tracer comprises a cannabinol molecule or a derivative of cannabinol molecules and a label coupled to the cannabinol molecule or the derivative of cannabinol molecules, wherein the derivative comprises at least two benzene rings of the cannabinol molecule, and wherein binding sites on the recognition molecule is substantially saturated with the tracer to form a recognition molecule-tracer complex;
exposing a sample suspected of containing tetrahydrocannabinoids to the recognition molecule-tracer complex; and
measuring the amount of label from synthetic tracers that has been displaced from the recognition molecule.

50. The method of claim 49 wherein the recognition molecule is selected from the group consisting of an antibody, a receptor that binds to $\Delta^9$-THC, and a receptor that binds to $\Delta^9$-THC metabolites.

51. The method of claim 50, wherein the antibody is capable of binding to $\Delta^9$-THC or its metabolites.

52. The method of claim 49, wherein the solid support is selected from the group consisting of a resin, a bead, and a wall of a column.

53. The method of claim 49, wherein the sample is an aqueous sample.

54. The method of claim 49, wherein the sample is a biological sample selected from the group consisting of saliva, whole blood, serum, plasma, hair, or urine.

55. The method of claim 49, wherein the step of exposing the sample to the recognition molecule-tracer complex further comprises the step of continuously flowing the sample past the recognition molecule-tracer complex under non-equilibrium conditions.

56. The method of claim 49 wherein the amount of displaced synthetic tracer is directly proportional to the concentration of $\Delta^9$-THC or its metabolites in the sample.

57. The method of claim 49 wherein the label is coupled to the cannabinol molecule or its derivatives at a position selected from the group of positions 1, 2, 3, 4, 5, 8, 9, and 10.

58. The method of claim 49 wherein the synthetic tracer has a general formula selected from the group consisting of:

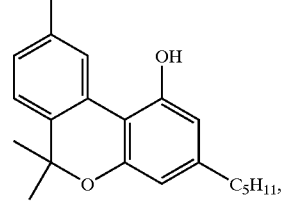

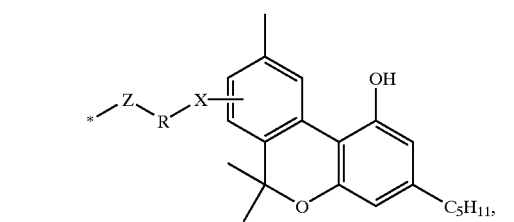

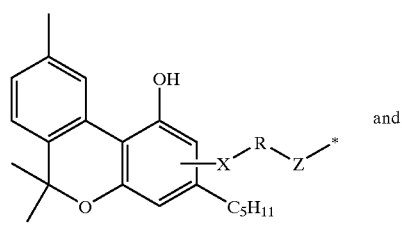

and

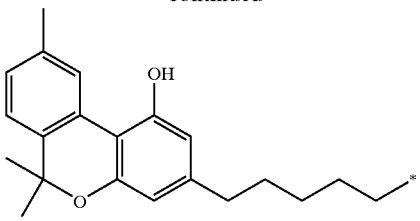

wherein
(a) R is an extending group,
(b) X and Z are reactive groups, and
(c)* is a label.

59. The method of claim 49 wherein R is selected from the group consisting of —(CH$_2$)n— and C(O)—(CH$_2$)nCO and wherein n may be from about zero to about 15.

60. The method of claim 49 wherein X or Z, or both, are selected from the group consisting of an imino, an iminocarbonyl, a carbonyl, a carbonimidoyl, an iminosulfonyl, a sulfonyl, an iminocarbonimidoyl, a thiocarbonyidlimino, an iminocarbonyloxy, an iminothiocarbonyloxy, a (sulfonyliminocarbonyl)diimino, a triazinyldiimino, ethylene diamine (EDA) or a succinimidyl active ester (OSu) group.

61. The method of claim 49 wherein the label is coupled to the cannabinol at position 9 and the synthetic tracer has a general formula:

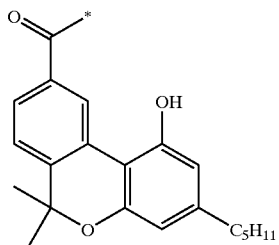

and wherein * is a label.

* * * * *